United States Patent [19]

Miller

[11] Patent Number: 4,628,943

[45] Date of Patent: Dec. 16, 1986

[54] BIPOLAR SCREW-IN PACKING LEAD ASSEMBLY

[75] Inventor: Sandra L. Miller, Miami, Fla.

[73] Assignee: Cordis Corporation, Miami, Fla.

[21] Appl. No.: 747,619

[22] Filed: Jun. 21, 1985

[51] Int. Cl.$^4$ .............................................. A61N 1/18
[52] U.S. Cl. ................................. 128/785; 128/419 P
[58] Field of Search ...................... 128/642, 785, 419 P

[56] References Cited

U.S. PATENT DOCUMENTS

| | | | |
|---|---|---|---|
| 3,974,834 | 8/1976 | Kane | 128/419 P |
| 4,010,758 | 3/1977 | Rockland et al. | 128/418 |
| 4,046,151 | 9/1977 | Rose | 128/404 |
| 4,106,512 | 8/1978 | Bisping | 128/418 |
| 4,357,946 | 11/1982 | Dutcher et al. | 128/419 P |
| 4,463,765 | 8/1984 | Gold | 128/419 P |
| 4,577,643 | 3/1986 | Beranek | 128/785 |

*Primary Examiner*—Kyle L. Howell
*Assistant Examiner*—Randy Citrin
*Attorney, Agent, or Firm*—Henry W. Collins; Thomas R. Vigil

[57] ABSTRACT

The bipolar screw-in pacing lead assembly is adapted to be mechanically secured to tissue of a body in an electrically conductive manner. The pacing lead assembly comprises an insulative tubular sheath having a distal end and a proximal end. First and second conductive members each having a distal end and a proximal end are received in and extend substantially the length of the tubular sheath. The first conductive member is insulated from the second conductive member. The pacing lead assembly further includes a distal electrode assembly at the distal end of the tubular sheath comprising a corkscrew attachment device which is electrically and mechanically connected to the second conductive member. A proximal terminal electrode assembly is coupled to the tubular sheath and includes (a) a cathode terminal pin/attachment member which is coupled by a brush contact to the second conductive member and which can be rotated to operate the corkscrew attachment device to secure the distal electrode assembly to tissue of the body and (b) a ring electrode having a brush contact adapted to make contact with the rotatable proximal end of the first conductive member.

10 Claims, 3 Drawing Figures

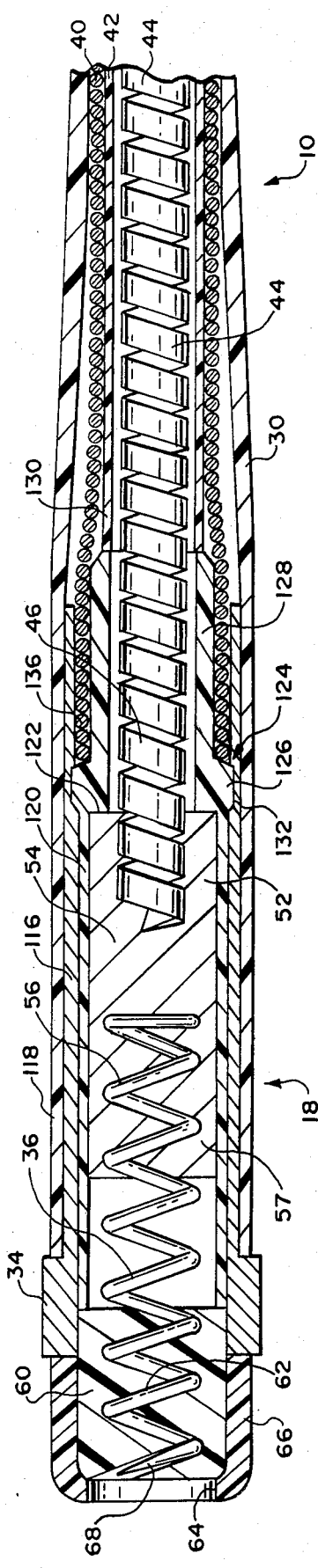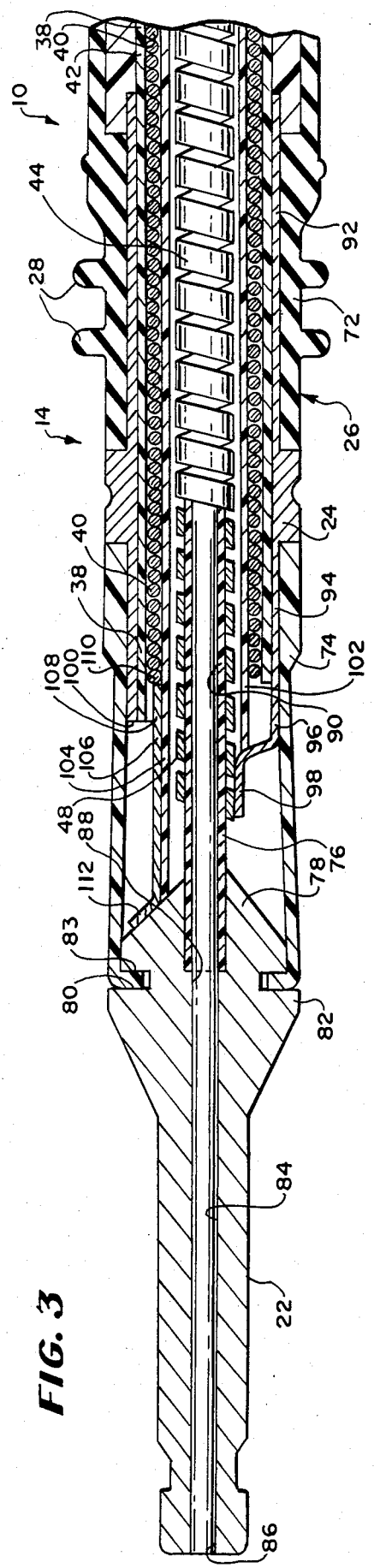

BIPOLAR SCREW-IN PACKING LEAD ASSEMBLY

BACKGROUND OF THE INVENTION

1. Field of the Invention

The present invention relates to a bipolar pacing lead, and more particularly, to a bipolar screw-in pacing lead assembly having a tip electrode assembly comprising a cathode electrode defined by a metal ring and an anode electrode defined by a corkscrew shaped securing device which is adapted to be threaded into living tissue for securing the electrode assembly to the living tissue and at the same form an anode electrically connected to the living tissue.

2. Description of the Prior Art

Heretofore various pacing lead assemblies having screw-in devices or other securing devices for securing a pacing lead assembly to living tissue have been proposed. Examples of such previously proposed pacing lead assemblies are disclosed in the following patents or patent publications:

| U.S. Pat. No. | Patentee |
|---|---|
| 3,253,595 | Murphy, Jr., et al. |
| 3,416,534 | Quinn |
| 3,472,234 | Tachick |
| 3,737,579 | Bolduc |
| 3,844,292 | Bolduc |
| 3,875,947 | Jula, et al. |
| 3,974,834 | Kane |
| 4,000,745 | Goldberg |
| 4,010,758 | Rockland, et al. |
| 4,026,301 | Friedman, et al. |
| 4,026,303 | Babotai |
| 4,046,151 | Rose |
| 4,106,512 | Bisping |
| 4,146,036 | Dutcher, et al. |
| 4,217,913 | Dutcher |
| 4,282,885 | Bisping |
| 4,311,153 | Smits |
| 4,357,946 | Dutcher, et al. |
| 4,381,013 | Dutcher |
| 4,452,254 | Goldberg |
| 4,463,765 | Gold |

The Murphy, Jr., et al. U.S. Pat. No. 3,253,595 discloses a cardiac pacer electrode system which includes two electrodes each having a projecting coil of platinum wire which can be inserted into a puncture wound made in a patient's heart.

The Quinn U.S. Pat. No. 3,416,534 discloses a body organ electrode which includes a helically wound conductor having a conductor tip which is sharpened to facilitate screwing into an organ which is to be electrically stimulated. The sharpened conductor tip is housed within the bore of a hypodermic needle so that once the needle has been inserted into the organ to be stimulated, the conductor is turned in order to advance the sharpened conductor tip into the organ tissue.

The Tachick U.S. Pat. No. 3,472,234 discloses a body organ electrode having a stiff helical sleeve positioned over an helically wound cable having a pointed tip and a key engageable, flattened conductor for facilitating screwing of the tip into an organ with a stylet.

The Bolduc U.S. Pat. No. 3,737,579 discloses a body tissue electrode and device for screwing the electrode into body tissue. The body implantable electrode comprises a flexible insulative conductor having a proximal end adapted for connection to a power supply and a distal end comprising an uninsulated, conductive, rigid helix adapted for attachment to body tissue. The device for screwing the electrode into body tissue is a tool which is cylindrically shaped and into which the insulated portion of the conductor is fitted so that the electrode comprising the rigid helix is securely held by the tool. Then, by applying a twisting rotation to the tool, the helical electrode may be screwed into the tissue.

The Bolduc U.S. Pat. No. 3,844,292 discloses an intravascular lead assembly having an electrically conductive barb at its distal end. The lead assembly is positioned within a cylindrical inner tube which, in turn, is positioned within a cylindrical outer tube and the lead assembly carried thereby is inserted into a body vessel. When the lead assembly is believed to be in a proper position in the heart, a plunger located at the proximal end of the lead assembly is depressed in order to move the inner tube and the lead assembly to a position where the barb just barely extends beyond an open end of the inner tube. Once it has been determined that the barb is in a satisfactory position, the plunger is further depressed in order to drive the barb a predetermined distance into the tissue of the heart.

The Jula, et al. U.S. Pat. No. 3,875,947 discloses a device for screwing a body tissue electrode into body tissue. The electrode is a rigid helical electrode which serves as the distal end portion of a conductor which may be screwed into body tissue. The electrode is screwed into body tissue with a device comprising a cylindrically shaped body which, once the helical electrode is positioned near the heart, is rotated in order to firmly screw the electrode into the heart.

The Kane U.S. Pat. No. 3,974,834 discloses a body implantable lead having a first electrode at its distal end comprising a rigid, electrically conductive helix with a sharp tip which is adapted to be screwed through tissue into a body organ and a second electrode which is in the form of a ring mounted on the lead just behind the first electrode. The lead has a bifurcated proximal end with each finger of the bifurcated end having a terminal pin extending therefrom.

The Goldberg U.S. Pat. No. 4,000,745 discloses an electrical lead for a cardiac stimulator and includes a helical member which may be screwed into the heart muscle. The electrical lead is attached or secured to the heart with an insertion tool comprising an elongated shaft having a beveled portion which is inserted between a turn in the helical wire and pushed into the electrical lead until the beveled end engages and grips a tapered portion of the lead.

The Rockland, et al. U.S. Pat. No. 4,010,758 discloses a bipolar body tissue electrode comprising a first helix-configured electrode adapted to be screwed into body tissue and a second disc shaped electrode disposed about the helical electrode for surface contact with the tissue. The first and second electrodes are connected to separate terminal pins in a bifurcated proximal end.

The Friedman, et al. U.S. Pat. No. 4,026,301 discloses an apparatus which includes a probe having a blunt, muscle-penetrating tip which is fitted with a sleeve so that the tip of the probe extends from the sleeve. A helical electrode is mounted on an elongated tool which is capable of imparting a rotational force to the electrode while allowing disengagement with the electrode in the direction of its longitudinal axis.

The Babotai U.S. Pat. No. 4,026,303 discloses an endocardial pacing electrode assembly comprising an electrode contained within a tube or casing and surrounded within the casing by a first spiral conductor which terminates at the distal end of the casing. A second spiral conductor is positioned surrounding the first spiral conductor and extends outside of the distal end of the casing to form a spiral pacing contact. The contact tip is not sharp, has no end points, and is round, continuous, and closes upon itself in a closed spiral configuration so that it can be screwed under the trabeculae or inner muscles of the heart without actually puncturing the heart.

The Rose U.S. Pat. No. 4,046,151 discloses a body implantable lead which has a stiffening stylet and which has a first helical electrode, a second ring electrode and two terminal pins in two proximal fingers connected respectively to the first and second electrodes in a manner as taught in the Kane U.S. Pat. No. 3,974,834.

The Dutcher, et al. U.S. Pat. No. 4,146,036 discloses a body implantable lead having a tissue securing member comprising a rigid, circular corkscrew or helix which extends beyond the end of a tip ring electrode in order to secure and maintain the ring electrode in engagement with endocardial tissue.

The Dutcher, et al. U.S. Pat. No. 4,217,913 discloses a body implantable lead and includes a helix or corkscrew which is electrically insulated from a electrode or electrically coupled to the electrode.

The Bisping U.S. Pat. No. 4,282,885 discloses an electrode assembly for implantation in the heart including an electrode lead and a helix protruding at the end of the electrode lead near the heart for screwing the electrode into cardiac tissue.

The Smits U.S. Pat. No. 4,311,153 discloses a screw-in lead having a lead tip with a sealing membrane through which a corkscrew electrode is rotated to engage heart tissue.

The Dutcher, et al. U.S. Pat. No. 4,357,946 discloses an epicardial pacing lead with stylet controlled helical fixation screw. The stylet controls a helical fixation screw in an electrode head of the pacing lead. The stylet is turned to advance the helical fixation screw laterally of the lead beyond the planar surface of the electrode head.

The Dutcher U.S. Pat. No. 4,381,013 discloses a removable stylet assembly comprising a first stylet portion including a straight wire with a curve at the distal end thereof, and a second stylet portion which is removable from the lead assembly and which includes a coil for transferring torque at the proximal end of the flexible coil to the distal end portion of the coil for implanting a corkscrew shaped electrode.

The Goldberg, et al. U.S. Pat. No. 4,452,254 discloses another form of screw-in tip electrode.

The Gold U.S. Pat. No. 4,463,765 discloses a pacing lead assembly, comprising a wire conductor extending within a tubular body and a corkscrew shaped securing device which is received in the tubular body and which has a proximal end fixed to a movable mounting member made of an insulative material in the tubular body. A drive mechanism in the form of a helical metal ribbon is received within the tubular body and extends from the proximal end of the lead to the distal end of the lead and is fixed to the other end of the mounting member. A terminal pin/drive member is positioned at the proximal end of the lead and has one end thereof connected to a proximal end of the ribbon and the other end thereof extending from the lead assembly. The terminal pin/drive member can be rotated to screw the securing device into living tissue in order to fix a separate distal electrode against cardiac tissue.

The West German Published Patent Application No. 28 06 069 discloses still another form of screw-in tip electrode.

As will be described in greater detail hereinafter, the bipolar screw-in lead assembly of the present invention differs from the various screw-in lead assemblies and similar lead attachment assemblies previously proposed by providing a tubular body having a distal electrode assembly at its distal end comprising a cathode electrode ring and an anode corkscrew shaped securing device which functions both as (a) means for securing the electrode assembly to the tissue of a heart and (b) means for establishing an anode electrical connection with the tissue. The anode electrode forming, corkscrew shaped securing device is electrically connected through a drive mechanism to an anode electrode ring in a single, finger-shaped, proximal terminal electrode assembly. A coiled wire conductor insulated from the drive mechanism is electrically connected to the cathode electrode ring at the distal end of the lead and to a terminal pin/drive member in the proximal electrode assembly which is adapted to be received in a terminal pin receiving socket in a pacer and which also can be rotated to drive the drive mechanism. The drive mechanism can be operated to rotate the corkscrew shaped securing device to secure the corkscrew securing device/anode electrode into cardiac tissue and at the same time place the cathode electrode ring against cardiac tissue in an electrically conductive manner. The terminal pin and the anode ring are received in and make electrical contact with electrical contact members in a socket in a pacer.

SUMMARY OF THE INVENTION

An endocardial bipolar lead assembly which is adapted to be placed in a body and which can be mechanically secured to body tissue in an electrically conductive manner. The lead assembly comprises an insulated tubular sheath having a proximal end and a distal end. A first conductor which has a proximal end and a distal end extends substantially the length of the tubular sheath. The first conductor is insulated from the second conductor. An electrode assembly is located at the distal end of the tubular sheath. The distal electrode assembly comprises a cathode ring electrode and a tissue-attachment anode electrode which has a proximal end and a distal end. The distal end of the first conductor is mechanically and electrically coupled to the proximal end of the tissue-attachment anode electrode. The distal end of the second conductive is electrically connected to the ring cathode electrode. The tissue-attachment anode electrode is capable of mechanically securing the distal electrode assembly to tissue of the body. The tissue-attachment anode electrode and the ring cathode electrode are in direct electrical contact with the body. A single finger-shaped proximal terminal electrode assembly includes a cathode terminal pin mechanically coupled to the first conductor. The cathode terminal pin is electrically isolated from the first conductor and is electrically coupled to the second conductor means. An anode ring on the terminal assembly is insulated from the cathode terminal pin and the second conductor. The anode ring is electrically coupled to the first conductor. The terminal pin is adapted to be coupled to a cathode of an electrical power source. The anode ring is adapted to be coupled to the anode of the electrical power source. The terminal pin is notated to mechanically activate the tissue-attachment anode electrode to secure the distal electrode assembly to tissue.

BRIEF DESCRIPTION OF THE DRAWINGS

FIG. 2 is an enlarged sectional view of the distal electrode assembly at the distal end of the pacing lead asssembly shown in FIG. 1 and shows the anode corkscrew electrode within the distal electrode assembly.

FIG. 3 is an enlarged sectional view of the proximal terminal electrode assembly at the proximal end of the pacing lead assembly shown in FIG. 1.

DESCRIPTION OF THE PREFERRED EMBODIMENT

Figure 1:
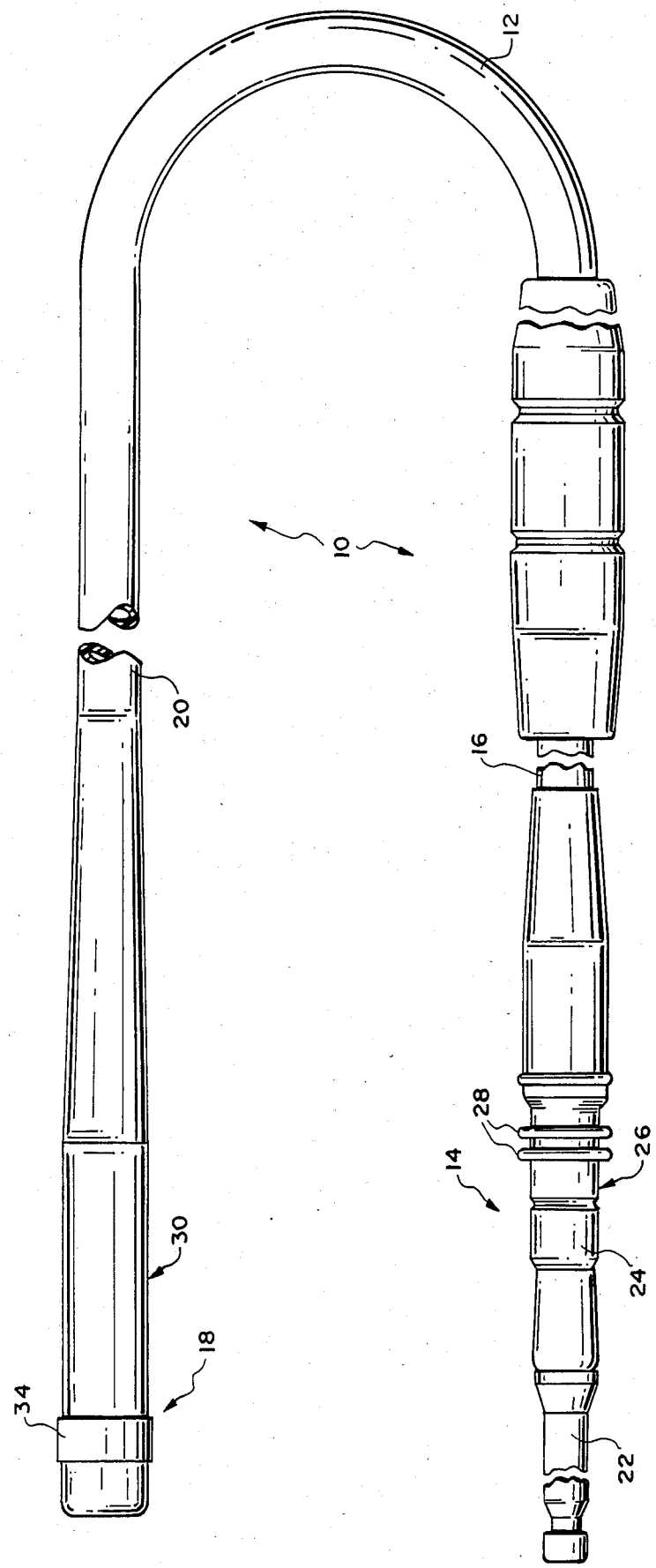
FIG. 1 is a plan view of the pacing lead assembly of the present invention with portions of the pacing lead cut away and shows (a) a simple, finger shaped proximal terminal electrode assembly including an electrical coupling and mechanical activating mechanism located at the proximal end of the pacing lead assembly and (b) a distal electrode assembly including a cathode ring electrode and a distal anode corkscrew electrode and securing device (hidden from view within the distal electrode assembly).

Referring now to the drawings in greater detail there is illustrated in FIG. 1 a bipolar screw-in pacing lead 10 constructed in accordance with the teachings of the present invention. The pacing lead 10 includes a lead body 12, a proximal terminal electrode assembly 14 located at the proximal end 16 of the lead body 12, and a distal electrode assembly 18 located at the distal end 20 of the lead body 12.

The terminal electrode assembly 14 is mounted to the proximal end 16 of the lead body 12 and includes a cathode electrode terminal pin/activating member 22 that is adapted to be plugged into a terminal pin receiving socket of a cardiac pacer (not shown).

The proximal terminal electrode assembly 14 has a single finger-like shape.

The proximal terminal electrode assembly 14 also includes an anode ring 24 mounted on a tubular housing 26 of the assembly 14. The tubular housing 26 is made of an insulating material and has annular sealing ribs or flanges 28 thereon.

The distal electrode assembly 18 includes a tubular member 30 which is made of an insulating material and which has a cathode ring electrode 34 mounted thereon or therein and a corkscrew securing device/anode electrode 36 (FIG. 2) received within the tubular member 30.

According to the teachings of the present invention and as will be described in greater detail hereinafter, the securing device 36 is electrically connected to the anode ring 24 and the cathode electrode ring 34 is electrically connected to the cathode electrode/terminal pin 22.

Turning now to FIGS. 2 and 3, the lead body 12 includes a first tubular sleeve or sheath 38 (FIG. 3) having a coiled wire conductor 40 therein. A second tubular sleeve or sheath 42 is received within the lumen of the coiled wire conductor 40.

Then a helically wound metal ribbon/drive member 44 having a distal end 46 (FIG. 2) and a proximal end 48 (FIG. 3) extends substantially the length of the lead body 12 within the lumen of the second sheath 42.

As shown in FIG. 2, the distal end 46 of the metal ribbon 44 is electrically and mechanically connected to the proximal end 52 of a cylindrical mounting member 54 which is made of an electrically conductive material and which is rotatably mounted within the distal electrode assembly 18. A proximal end 56 of the securing device 36 is mounted to a distal end 57 of the mounting member 54 in an electrically conductive manner and is rotatable when the mounting member 54 is caused to rotate as a result of the metal ribbon 44 being rotated.

When the metal ribbon 44 is rotated, the securing device 36 is rotated in a forward direction through a fixed, fluid tight plug 60 made of an insulative material and more specifically through a spiral passageway 62 extending through the plug 60 which has a portion thereof received within the ring electrode 34.

In this way, when the securing device 36 is rotated by the metal ribbon 44, as heretofore described, the securing device 36 is rotated through the passageway 62 in a screw like manner and exits the passageway 62 through an opening 64 in an insulative tip member 66 fixed about the plug 60 in front of the ring electrode 34 so that a sharpened distal end 68 of the securing device 36 can be implanted into tissue of the ventricle or atrium of a heart.

Referring now to FIG. 3, the proximal end 48 of the metal ribbon 44 terminates within the proximal assembly 14, and more particularly within the tubular housing 26 comprising an insulative sleeve 72, the anode ring electrode 24 and a tubular insulative member 74. The proximal end 48 of the metal ribbon 44 is received over and fixed to an insulative tubing 76. The tubing 76 is fixed to a distal end portion 78 of the terminal pin/activating member 22 such that rotation of the pin 22 causes rotation of the tubing 76 to rotate the metal ribbon 44. It will be noted that the tubing 76 insulates the terminal pin/activating member 22 from the metal ribbon 44.

The distal end portion 78 of the terminal pin/activating member 22 is cone shaped and includes an annular groove 80 at a base 82 thereof into which an inwardly extending flange or end wall 83 of the tubular insulative member 74 is rotatably received. In this way the terminal pin/activating member 22 is permitted to rotate relative to the tubular housing 26 to rotate the metal ribbon 44.

The terminal pin/activating member 22 also has an axial passageway 84 which is open at a proximal end 86 of the terminal pin/activating member 22 and at a forward end 88 which is coaxial with the tubing 76. The forward end 88 of the passageway 84 is also coaxial with a lumen 90 defined within the metal ribbon 44 so that a stylet (not shown) can be inserted through the rear end 86 of the passageway 84 in the terminal pin/activating member 22 and into the lumen 90 of the metal ribbon 44 for stiffening of the pacing lead 10 when the pacing lead 10 is inserted into a body, such as into a vein, and/or for positioning the electrode assembly 18 in the ventricle or the atrium of a heart.

As shown, the anode ring 24 makes contact with or is integral with a first metal sleeve portion 92 which extends into the insulative sleeve 72 and a second metal sleeve portion 94 which extends into the tubular insulative member 74.

The sleeve portion 94 has a tab 96 extending rearwardly therefrom with a bent radially inwardly offset end portion 98 which makes a wiping or brush contact with the proximal end 48 of the metal ribbon 44.

In this way, a conductive path is established from anode ring 24 through sleeve portion 94, tab 96, brush contact/end portion 98, metal ribbon 44 and cylindrical electrically conductive mounting member 54 to the anode electrode/corkscrew securing device 36.

It will be apparent from FIG. 3 that the first insulative sheath 38 extends to a proximal end 100 of the sleeve portion 94 opposite the tab 96. Then the second insulative sheath 42 has a portion 102 that extends to the offset end portion 98 on one side and a portion 104 that extends to the cone shaped forward end portion 78 of the terminal pin 22 on the other side.

As shown, a leaf metal contact member 106 has one end 108 received between the sheaths or tubings 38 and 42 and fixed, such as by solder or weld, to a proximal end 110 of the coiled wire condutor 40. Preferably, the contact member 106 is also fixed, such as by an adhesive, to the sheath portion 104 of the sheath 42 better to fix the contact member 106 in the position shown.

The leaf contact member 106 has a radially outwardly bent, brush forming end portion 112 which makes a wiping or brush contact with the cone shaped forward end portion 78 of the terminal pin 22.

Referring again to FIG. 2, the cathode electrode ring 34 is received over part of the plug 60 and has an integral rearwardly extending sleeve portion 116 which extends into a distal portion 118 of the insulated tubular member 30.

As shown in FIG. 2, the distal electrode assembly 18 further includes an internal insulative tubular sleeve member 120 which has a forward or distal sleeve portion that is situated within the ring electrode 34 and sleeve 116 up to the plug 60. The conductive cylindrical member 54 is received in this insulative forward sleeve portion which has at its inner end an internal annular shoulder 122 which limits rearward movement of the cylindrical member 54.

The tubular sleeve member 120 further has a rearwardly extending hub portion 124 including an annular rib 126 which is larger in diameter than the sleeve portion 122 and a barrel portion 128 which is smaller in diameter than the sleeve portion 122 and which extends rearwardly to a distal end 130 of the inner, second tubing or sheath 42.

The sleeve 116 has a stepped proximal end portion 132 which has an inner diameter larger than the inner diameter of the forward portion of the sleeve 116. The rib 126 is received in the end portion 132 against the stepped portion of the sleeve 116 with an annular space defined between sleeve end portion 132 and barrel portion 128 for receiving, preferably with an interference fit, a distal end 136 of the coiled wire conductor 40 which makes a good mechanical and electrical connection with the end portion 132 of the sleeve 116 integral with the cathode ring electrode 34.

In this way, a conductive path is established from the cathode ring electrode 34 through sleeve 116, coiled wire conductor 40, leaf contact member 110, brush end portion 112, and cone forward end portion 78 to terminal pin 22.

Rotation of terminal pin/actuating member 22 causes rotation and fixing of the corkscrew securing device 36 into an atrium or ventricle of a heart after the lead 10 has been implanted. This establishes an anode connection to the heart tissue. Then a cathode connection is established from terminal pin 22 to ring electrode 34 with the anode connection being from anode ring 24 to anode electrode/securing device 36 such that a conventional cathode connection of proximal cathode terminal pin 22 to distal cathode ring electrode 34 is maintained while at the same time establishing an anode electrode connection from the anode ring 24 to the corkscrew securing device 36.

From the foregoing description it will be appreciated that the bipolar screw-in pacing lead assembly 10 of the present invention has a number of advantages, some of which have been described above and others of which are inherent in the invention.

In particular, a cathode connection is provided from the annular electrode member 34 to the terminal pin 22, and at the same time an anode connection is provided from the securing device 36 to the anode ring 24 with the cathodic terminal pin being rotatable to implant the anodic corkscrew securing device 36.

It will also be apparent that modifications can be made to the bipolar screw-in pacing lead assembly of the present invention without departing from the teachings of the present invention. Accordingly, the scope of the invention is only to be limited as necessitated by the accompanying claims.

I claim:

1. An endocardial bipolar lead assembly which is adapted to be placed in a body through a blood vessel and which is adapted to be mechanically secured to tissue of the body in an electrically conductive manner, said lead assembly comprising:

an insulated tubular sheath, said tubular sheath having a distal end and a proximal end;

first and second conductive means, said first conductive means having a distal end and a proximal end, said first conductive means extending substantially the length of said tubular sheath, said second conductive means having a distal end and a proximal end, said second conductive means extending substantially the length of said tubular sheath and said first conductive means being insulated from said second conductive means;

an electrode assembly located at said distal end of said tubular sheath;

said distal electrode assembly comprising a ring cathode electrode and a tissue-attachment anode electrode member, said tissue-attachment anode electrode having a distal end and a proximal end, said distal end of said first conductive means being mechanically and electrically coupled to said proximal end of said tissue-attachment anode electrode member, said distal end of said second conductive means being electrically connected to said ring cathode electrode, said tissue-attachment anode electrode member being capable of mechanically securing said distal electrode assembly to tissue of a body with said tissue-attachment anode electrode member and said ring cathode electrode adapted to be in direct electrical contact with tissue of the body;

a single finger-shaped proximal terminal electrode assembly including cathode terminal pin means mechanically coupled to said first conductive means, said terminal pin means being electrically isolated from said first conductive means, said terminal pin means being electrically coupled to said second conductive means, and an anode ring on said assembly insulated from said cathode terminal pin means and said second conductive means, said anode ring being electrically coupled to said first conductive means, said terminal pin means being adapted to be coupled to a cathode of an electrical power source and said anode ring being adapted to be coupled with an anode of the electrical power source, and activating means including at least a portion of said single finger-shaped proximal terminal electrode assembly for mechanically activating said tissue-attachment anode electrode member for securing said distal electrode assembly to tissue.

2. The assembly of claim 1 wherein said distal electrode assembly includes an insulating tubular sleeve member and said proximal end of said tissue-attachment anode electrode member is electrically and mechanically coupled to said distal end of said first conductive means by an electrically conductive mounting member, said electrically conductive mounting member being rotatable within said insulating tubular sleeve member.

3. The assembly of claim 2 wherein said second conductive means comprise a coiled wire conductor and said ring cathode electrode has a sleeve portion extending rearwardly on the outside of said insulating tubular sleeve member, and said sleeve portion is electrically coupled to said distal end of said coiled wire conductor.

4. The assembly of claim 2 wherein said tissue-attachment anode electrode member comprises a corkscrew-shaped securing device having a proximal end and a distal end, said corkscrew-shaped device being secured to said electrically conductive mounting member and rotatable therewith.

5. The assembly of claim 4 wherein said distal electrode assembly includes an insulative plug mounted at a forward end of said insulative tubular sleeve member, said insulative plug having a helically-shaped passageway therein and said corkscrew-shaped tissue-attachment anode electrode member is received within said helically-shaped passageway of said insulative plug member.

6. The assembly of claim 2 wherein said first conductive means comprise a flat, helically-wound metal ribbon, said distal end of said metal ribbon being electrically and mechanically coupled to said electrically conductive mounting member and rotatable therewith.

7. The assembly of claim 6 wherein said proximal electrode assembly includes said anode ring and brush contact means coupled to said anode ring and in wiping or brush contact with said proximal end of said metal ribbon.

8. The assembly of claim 6 including a second and inner tubular sheath and said second conductive means is a helically wound wire conductor positioned between said inner and outer tubular sheaths, said metal ribbon extending within said inner tubular sheath and said distal end of said second conductive means being electrically coupled to said ring cathode electrode.

9. The assembly of claim 6 wherein said terminal pin means and said activating means include a terminal pin adapted to be received by a cathode terminal pin receiving socket of a pacer, said cathode terminal pin being mounted for rotation relative to said terminal electrode assembly, and said activating means further includes an insulative tubing coupled between a forward end of said terminal pin and said proximal end of said metal ribbon whereby rotation of said cathode terminal pin rotates said metal ribbon and said tissue-attachment anode electrode member to attach same to tissue of a body.

10. The assembly of claim 9 wherein said second conductive means is a coiled wire conductor having a proximal end received in said proximal terminal electrode assembly, said cathode terminal pin having a forward end exposed within said terminal electrode assembly, and said terminal electrode assembly including brush means which are coupled to the proximal end of said coiled wire conductor and which makes a brush contact with said internally exposed forward end of said cathode terminal pin.

* * * * *

UNITED STATES PATENT AND TRADEMARK OFFICE
CERTIFICATE OF CORRECTION

PATENT NO. : 4,628,943

DATED : December 16, 1986

INVENTOR(S) : Sandra L. Miller

It is certified that error appears in the above-identified patent and that said Letters Patent is hereby corrected as shown below:

On the cover page, title of the invention should read -- Bipolar Screw-In Pacing Lead Assembly --.

Signed and Sealed this

Fourteenth Day of April, 1987

*Attest:*

DONALD J. QUIGG

*Attesting Officer*   *Commissioner of Patents and Trademarks*